United States Patent [19]

Buchnea

[11] E Re. 30,884

[45] Reissued Mar. 16, 1982

[54] ON-LINE SYSTEM FOR MONITORING SHEET MATERIAL ADDITIVES

[75] Inventor: Alexander Buchnea, Downsview, Canada

[73] Assignee: Sentrol Systems Ltd., Downsview, Canada

[21] Appl. No.: 119,389

[22] Filed: Feb. 7, 1980

Related U.S. Patent Documents

Reissue of:

[64] Patent No.: 4,081,676
Issued: Mar. 28, 1978
Appl. No.: 751,312
Filed: Dec. 17, 1976

[51] Int. Cl.[3] ..... G01N 23/223

[52] U.S. Cl. ..... 250/272; 250/277 R

[58] Field of Search ..... 250/272, 359, 358 R, 250/273, 277 R

[56] References Cited

U.S. PATENT DOCUMENTS

| | | | |
|---|---|---|---|
| 3,660,662 | 5/1972 | Puolakka | 250/272 X |
| 3,749,910 | 7/1973 | Carr-Brion et al. | 250/272 X |
| 3,904,876 | 9/1975 | Arendt | 250/359 |
| 3,928,765 | 12/1975 | Teller | 250/272 |

FOREIGN PATENT DOCUMENTS 793301 4/1958 United Kingdom .

*Primary Examiner*—Alfred E. Smith
*Assistant Examiner*—Carolyn E. Fields
*Attorney, Agent, or Firm*—Shenier & O'Connor

[57] ABSTRACT

An on-line system for determining the content, in a sheet material such as a paper web, of one or more additives such as titanium dioxide exhibiting relatively high-energy X-ray fluorescence and of an additive such as clay exhibiting relatively low-energy X-ray fluorescence. The sheet is irradiated with X-ray radiation of sufficiently high energy to cause the high-energy fluorescence additives to emit fluorescent radiation. Fluorescence intensity signals are generated as a function of the intensity of the fluorescent radiation from the high-energy fluorescence additives, and an absorption signal is generated as a function of the radiation passing through the sheet material without being absorbed. The fluorescence intensity signals are used to determine the content of the high-energy fluorescence additives and to determine the expected absorption of the exciting radiation by the material with the determined contents of those additives. The expected absorption is compared with the actual absorption as indicated by the absorption signal to determine the content of the low-energy fluorescence additive. In determining the content of the high-energy fluorescence additives, compensation is provided for basis weight, moisture, and the presence of the other additives. Basis weight and moisture compensation is also provided in determining the content of the low-energy fluorescence additive.

15 Claims, 3 Drawing Figures

ON-LINE SYSTEM FOR MONITORING SHEET MATERIAL ADDITIVES

Matter enclosed in heavy brackets [ ] appears in the original patent but forms no part of this reissue specification; matter printed in italics indicates the additions made by reissue.

BACKGROUND OF THE INVENTION

This invention relates to a system for continuously monitoring the contents of the individual constituents of a sheet material and, more particularly, to a system for monitoring the contents of the constituents of a paper web.

Various additives such as titanium oxide ($TiO_2$), calcium carbonate (CaCO), and clay or kaolin ($Al_2O_3.2SiO_2.2H_2O$) are often used to improve such paper qualities as brightness and opacity. Considerations of cost and quality control make it desirable that the concentrations of these additives, collectively referred to as "ash", be continuously monitored. Prior attempts to develop on-line monitoring have proven to be deficient in one or more respects. Thus, devices using preferential absorption of gamma rays or backscattering of beta particles to measure total ash content are subject to inaccuracies resulting from variations in the relative concentrations of the ash constituents. A recent device using preferential X-ray absorption attempts to avoid this problem by choosing the X-ray energy such that the absorption coefficients of clay and $TiO_2$ are equal. This approach, too, has drawbacks. First, the X-ray energy selected is just below the K-absorption edge of titanium, so that only a slight variation in the X-ray energy will produce a large and misleading variation in the measured absorption coefficient. Secondly, since it is not possible to obtain equal absorption coefficients for $TiO_2$, $CaCO_3$, and clay at the same X-ray energy level, the presence of $CaCO_3$ cannot be measured by this system and would in fact introduce error. Finally, this system is only capable of measuring the total ash content and cannot separately measure the clay content and the $TiO_2$ content. Individual monitoring and control is important, however, since $TiO_2$ is considerably more expensive than clay.

SUMMARY OF THE INVENTION

One of the objects of my invention is to provide a system for monitoring the contents of sheet material additives which individually monitors the contents of the various additives.

Another object of my invention is to provide a system which can monitor an additive exhibiting relatively low-energy fluorescence.

Still another object of my invention is to provide a system which is relatively insensitive to variations in source radiation energy.

A further object of my invention is to provide a system which can monitor the content of calcium carbonate.

Another object of my invention is to provide a system which can monitor the content of titanium dioxide.

Still a further object of my invention is to provide a system which is relatively insensitive to variations in sheet properties other than the property being measured.

Other and further objects will be found in the following description.

In general, my invention contemplates a system for determining the content of a first, high-energy fluorescence additive and a second additive in a sheet material in which the sheet is irradiated with X-ray radiation of sufficiently high energy to cause the first additive to emit fluorescent radiation. A first signal is generated as a function of the intensity of the fluorescent radiation, while a second signal is generated as a function of the absorption by the sheet material of a beam of X-ray radiation passing through the material. The energy of the beam is selected such that the beam is unequally or preferentially absorbed by the base material of the sheet material and the second additive. Preferably, the same beam source is used to induce fluorescent radiation from the material and to result in the absorption measurement. The first signal is used to determine the content of the first additive and to determine the expected absorption of the beam of radiation by the sheet of material with the determined content of the first additive. The expected absorption is compared with the actual absorption as indicated by the second signal to determine the content of the second additive.

My system thus allows the individual on-line monitoring of sheet material additives, one of which has too low an atomic number to allow direct measurement by fluorescence. Moreover, the system may be extended to permit the monitoring of any number of high-energy (>2KeV) fluorescence additives, such as calcium carbonate and titanium dioxide, simply by measuring the fluorescent radiation from the individual additives and taking all the additives into account when determining the expected absorption of the sheet material. Unlike systems of the prior art, my system does not require an absorption measurement near any critical point in the absorption spectrum of a constituent and thus is insensitive to small variations in the energy level of the radiation source.

In its preferred form, my system uses an iterative technique to correct the content determination of each of the high-energy fluorescence additives for the presence of other additives. Thus, for a paper web, initial determinations of calcium content and titanium content are made on the basis of the other additive content determinations obtained, for example, on the previous count. These initial calcium content and titanium content determinations are then used to arrive at an initial clay content determination. Corrected calcium content and titanium content determinations are then made on the basis of the initial content determinations, and the process is repeated until the desired accuracy is obtained. Each final content determination is thus relatively insensitive to variations in the content of the other constituents. Preferably, the system also receives inputs from a basis weight gauge and a moisture gauge to provide corrections for variations in these sheet material properties.

BRIEF DESCRIPTION OF THE DRAWINGS

In the accompanying drawings which form part of the instant specification and which are to be read in conjunction therewith and in which like reference numerals are used to indicate like parts in the various views:

FIG. 3 is a schematic view of the signal-processing portion of my system.

DETAILED DESCRIPTION OF THE PREFERRED EMBODIMENTS

Figure 1:
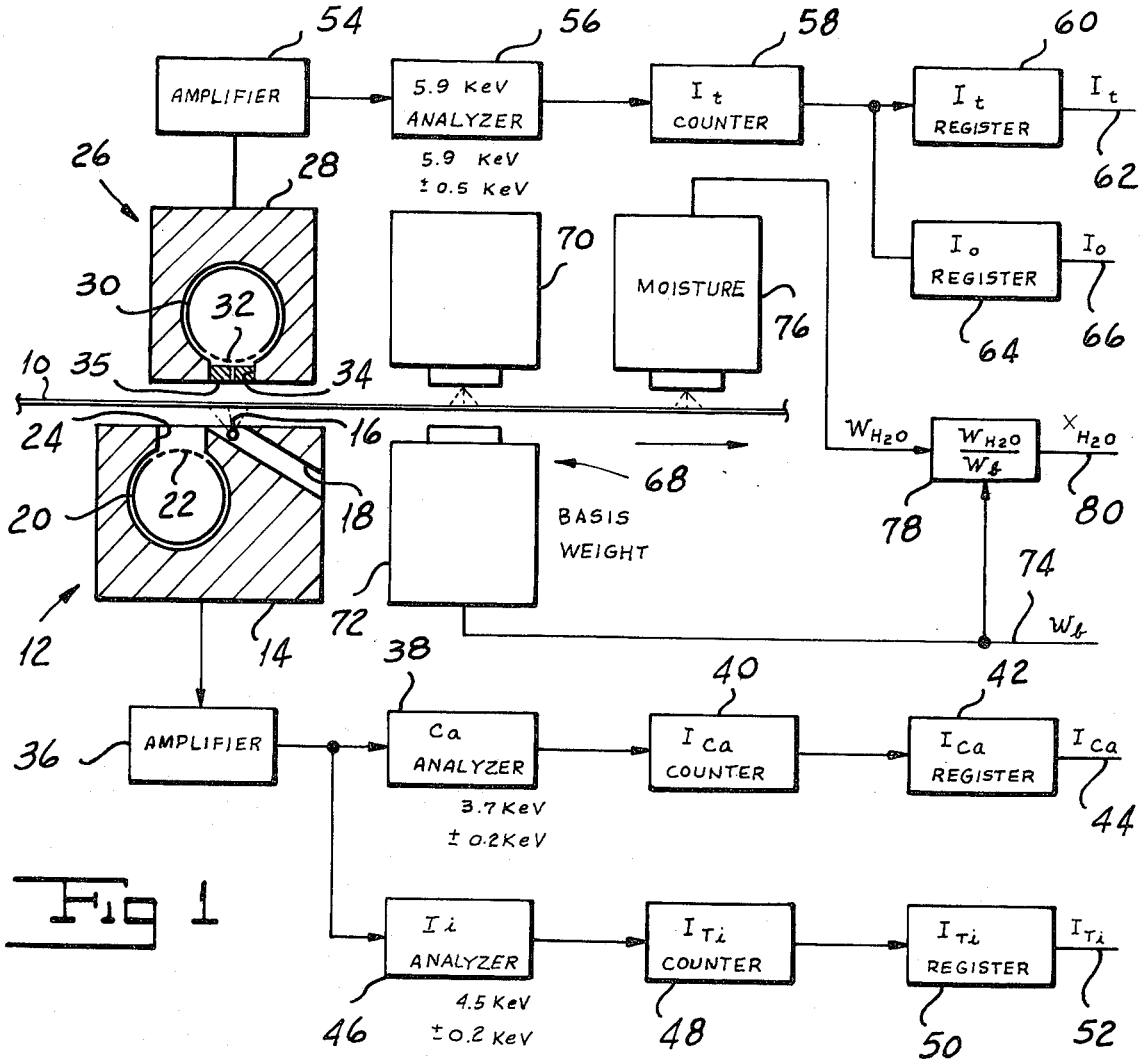
FIG. 1 is a partly schematic side elevation, shown partly in section, of the sensing and pulse-handling portions of my system.

Referring to FIG. 1, a web 10 of paper having a cellulose base is arranged to move between a fluorescent X-ray detector 12, which senses fluorescent radiation emitted from the web 10, and a primary X-ray detector 26, which senses primary radiation transmitted through the web 10. Each of the detectors 12 and 26 may be of any type known to the art, such as a Reuter-Stokes Model RSG-61 krypton-filled proportional counter. In the detector 12, a gas-filled proportional chamber 20, surrounded by a block of lead shielding 14, communicates with the web 10 via a beryllium window 22 forming part of the wall of the chamber 20 and registering with an aperture 24 formed in the block 14. Detector 12, which has a 130° acceptance angle, is preferably placed from 6 to 12 millimeters from the web 10, since it is relatively insensitive to web flutter within this range.

A source 16, disposed in a bore 18 formed in the block 14, directs X-ray radiation onto the web 10 from the same side as the chamber 20. The lead shielding 14 shields the proportional chamber 20 from direct radiation from the source 16. Preferably, I use $^{55}Fe$ as a source of X-ray radiation. It is to be understood that I use the term "X-ray radiation" in a generic sense to include gamma radiation. The 5.9 KeV photon emission of the source 16 following electron capture decay is highly efficient in stimulating fluorescent emission from the calcium and titanium in the web 10, since the energy level of the source emission is just above the K-absorption edges of both of these elements. The 5.9 KeV radiation is also well suited for the preferential absorption measurement, since the absorption coefficients of the constituents of the paper web 10 differ considerably from one another at this energy level.

Any calcium contained in the web 10 as part of the compound $CaCO_3$ will emit a characteristic fluorescent radiation of 3.7 KeV when stimulated by the 5.9 KeV source 16. Similarly, any titanium contained in the web 10 as part of the compound $TiO_2$ will emit a characteristic fluorescent radiation of 4.5 KeV in response to the 5.9 KeV excitation. Photons making up this fluorescent radiation impinge on the proportional chamber 20 to generate electrical pulses proportional in height to the energy of the emitted photons.

I feed the output from chamber 20 to an amplifier 36 which drives a conventional pulse height analyzer 38 having an energy window corresponding to the characteristic energy level of calcium fluorescence radiation, or 3.7 KeV. Preferably, analyzer 38 has a pass band between 3.5 KeV and 3.9 KeV to ensure an optimum signal-to-noise ratio. The analyzer 38 drives a digital counter 40 which counts the pulses corresponding to calcium fluorescent radiation during the counting period. Counter 40 in turn drives a register 42, the output of which appears on a line 44. Line 44 provides an $I_{Ca}$ signal representing the measured intensity of the calcium fluorescence radiation.

Amplifier 36 also drives a second pulse height analyzer 46 which has an energy window corresponding to the energy level of titanium fluorescent radiation, or 4.5 KeV. Preferably, the pass band of analyzer 46 extends from 4.3 KeV to 4.7 KeV. Analyzer 46 drives a counter 48 which in turn is coupled to a register 50. The output of register 50 appears on a line 52. Line 52 provides an $I_{Ti}$ signal representing the measured intensity of the titanium fluorescence radiation.

In the primary X-ray detector 26 a second proportional chamber 30 is arranged within a block 28 of lead shielding. Proportional chamber 30 communicates with the web 10 via a beryllium window 32 which registers with an aperture 34 formed in the block 28. Preferably, the primary X-ray detector 26 is arranged directly opposite the radiation source 16. A collimator 35 ensures that only normally exiting photons from the web 10 impinge on the proportional chamber 30.

An amplifier 54 coupled to the output of detector 26 drives a pulse height analyzer 56 having an energy window corresponding to the energy level of the incident radiation, or 5.9 KeV. Preferably, the pass band of the energy window extends from 5.4 KeV to 6.4 KeV. The pulse output of analyzer 56 drives a counter 58. Counter 58 drives a first register 60 having an output line 62 and a second register 64 having an output line 66. Line 62 provides an $I_t$ signal representing the measured intensity of the source radiation transmitted through the web 10.

The contents of counters 40, 48, and 58 are periodically transferred to the respective registers 42, 50, and 60, and the counters are then reset. The period over which each successive count is taken depends on the strength of the radiation source 16 and the desired statistical accuracy. With a source 16 having a strength of 10 mCi, for example, the statistical error for a counting period of 10 seconds is less than 1 percent.

Because of the relatively short half-life (2.6 years) of the $^{55}Fe$ radiation source 16, it is necessary to periodically provide an updated source intensity measurement with which to normalize the raw measurements on lines 44, 52, and 62. I accomplish this in the system shown in FIG. 1 by obtaining a count from the counter 58 during a calibration cycle in which the web 10 is removed from the gap separating the source 16 and the detector 26. At the end of the calibration count, the contents of counter 58 are transferred to register 64, which provides an $I_O$ signal on line 66 indicating the measured source intensity.

A basis weight gauge, indicated generally by the reference numeral 68, is disposed adjacent the web 10, preferably near the detectors 12 and 26. The basis weight gauge 68 may be of any suitable type known to the art, such as a beta absorption gauge comprising a beta ray source 70 and a beta ray detector 72 placed on opposite sides of the sheet 10. Suitable gauges are shown and described in U.S. Pat. No. 3,027,459, issued to Alcock et al, and U.S. Pat. No. 2,675,843, issued to Leighton et al. The basis weight gauge 68 provides a basis weight signal $W_b$ on line 74, indicating the basis weight or total mass per unit area of the web 10. A moisture gauge 76 disposed adjacent the web 10, preferably near the basis weight gauge 68 and the detectors 12 and 26, provides an output indicating the absolute moisture content of the web 10. A suitable moisture gauge is the infrared gauge described in U.S. Pat. No. 3,150,264, issued to Ehlert. The output of the gauge 76 is fed to the numerator input of a divider circuit 78, the denominator input of which is supplied from the basis weight line 74. Divider 78 thus provides an output on line 80 representing the relative or fractional moisture $X_{H2O}$ of the web 10.

Figure 2:
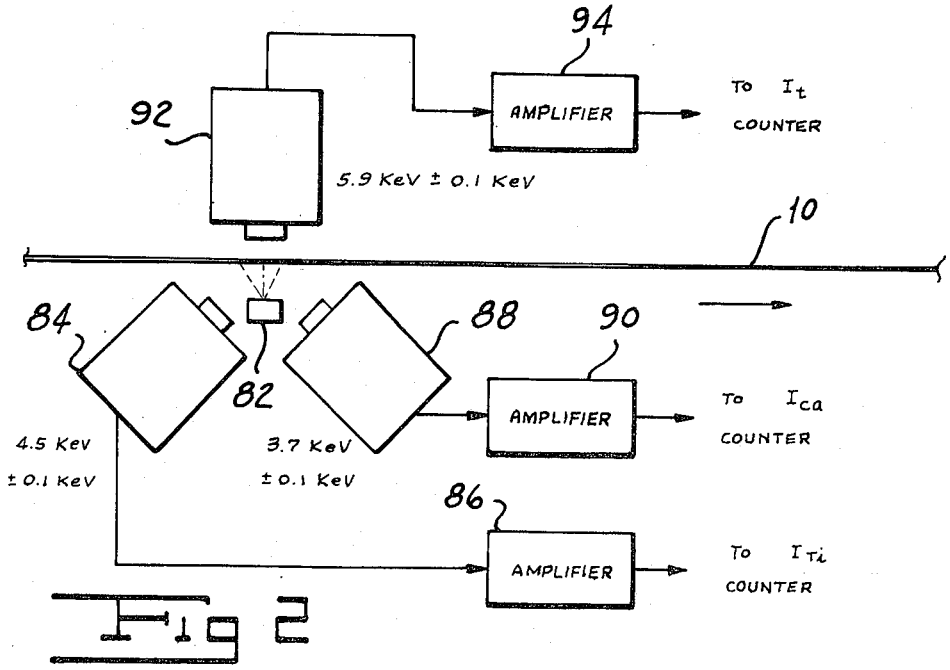
FIG. 2 is a partly schematic side elevation of an alternative sensing portion for the system shown in FIG. 1.
Figure 1:
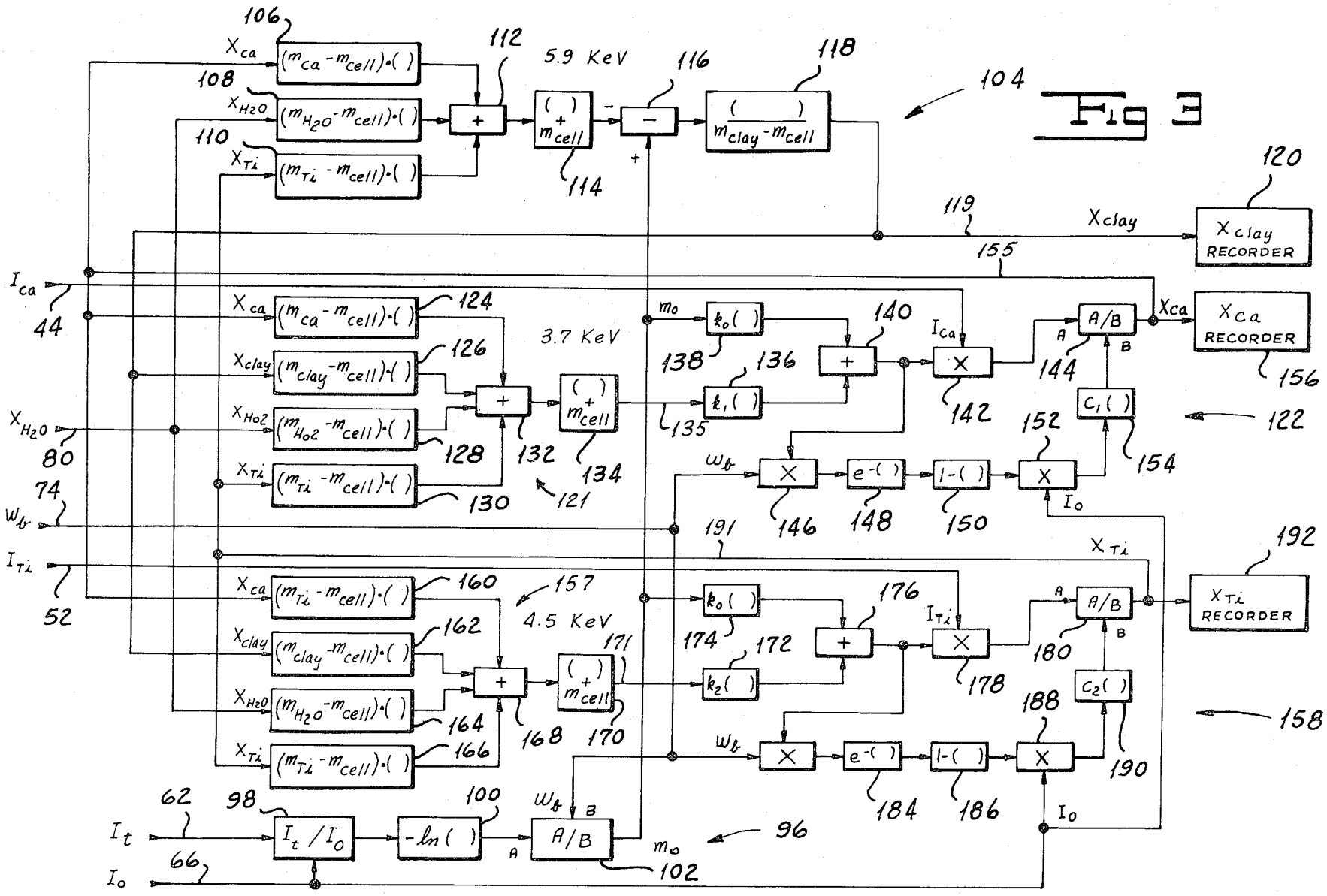

Proportional counter X-ray detectors of the type shown in FIG. 1 result in some smearing of the fluorescence bands of interest where both calcium and titanium are present in the web 10. Thus, the output pulses from amplifier 66 corresponding to the calcium fluorescence radiation and the titanium fluorescence radiation will overlap somewhat in height, causing a small amount of error. This error may be reduced somewhat by centering the energy windows of the pulse height analyzers 38 and 46 on the outside shoulders rather than the peaks of the respective emission curves. Alternatively, separate solid-state detectors such as shown in FIG. 2 may be used. In the embodiment shown in FIG. 2, a radiation source 82 comprising {Fe directs 5.9 KeV radiation toward one side of the paper web 10. A pair of solid-state detectors 84 and 88, arranged on the same side of the web 10 as the radiation source 82, sense fluorescent radiation emitted from the web 10. Detector 84 is responsive to 4.5 KeV fluorescent radiation emitted by the titanium in the web 10, while detector 88 is responsive to 3.7 KeV fluorescent radiation from the calcium in the web 10.

I couple detectors 84 and 88 to respective amplifiers 86 and 90 which drive suitable counters, such as the counters 40 and 48 shown in FIG. 1. A third solid-state detector 92 disposed on the other side of the web 10 is responsive to 5.9 KeV source radiation transmitted through the web 10. Detector 92 is coupled to an amplifier 94 which in turn drives a suitable counter such as the counter 58 shown in FIG. 1. Detectors 84, 88, and 92 may be Si(Li) detectors, for example, which have a resolution of 0.1 to 0.2 KeV. Since these detectors require liquid nitrogen cooling, a preferable choice for such applications as paper mills may be cadmium telluride, or CdTe, detectors, which can operate at room temperature. While I have shown individual detectors 84 and 88 for purposes of clarity, it is to be understood that in practice a single instrument is used to provide the same measurements.

Preferably, the arrangement of FIG. 1 is made up of digital components having multibit parallel inputs and outputs. For purposes of clarity, I have indicated single-line inputs and outputs.

I use an iterative technique in my system to determine the additive contents from the various raw measurements produced by the apparatus shown in FIG. 1. By way of exposition, I have outlined below the governing constituent relations involved in this technique. First, the absorption coefficient m of the web 10 is defined, for a given X-ray energy E, by the relationship:

$$[m=(-1/W_b)\ln(I_t/I_0)]\ m=(-1/W_b)\ln(I_t/I_0) \tag{1}$$

where $W_b$ is the basis weight or total mass per unit area of the web 10, $I_0$ is the intensity of normally incident, monochromatic radiation of energy E, and $I_t$ is the intensity of the incident radiation transmitted through the web 10. In the embodiment shown in FIG. 1, $I_0$ and $I_t$ correspond respectively to the count of counter 58 with web 10 removed and to the count with the web 10 in place between the radiation source 16 and the detector 26.

The absorption coefficient of the web 10 is equal to the weighted average of the absorption coefficients of the web constituents. Thus, for a web containing $CaCO_3$, clay, water, $TiO_2$, and cellulose:

$$m=X_{Ca}m_{Ca}+X_{Clay}m_{Clay}+X_{H2O}m_{H2O}+X_{Ti}m_{Ti}+X_{Cell}m_{Cell}, \tag{2}$$

where $X_{Ca}$, $X_{Clay}$, $X_{H2O}$, $X_{Ti}$, and $X_{Cell}$ are the fractional contents by weight, and $m_{Ca}$, $m_{Clay}$, $m_{H2O}$, $m_{Ti}$, and $m_{Cell}$ are the mass absorption coefficients, of the respective web constituents at energy E.

Since for a web containing only these constituents:

$$[X_{Ca}+X_{Clay}+X_{H2O}+X_{Ti}+X_{cell}=1,]\ X_{Ca}+X_{Clay}+X_{H2O}+X_n+X_{cell}=1, \tag{3}$$

$X_{cell}$ can be eliminated as a variable and equation (2) can be rewritten in the form:

$$m=m_{cell}+X_{Ca}(m_{Ca}-m_{cell})+X_{Clay}(m_{Clay}-m_{cell})+X_{H2O}(m_{H2O}-m_{cell})+X_{Ti}(m_{Ti}-m_{cell}). \tag{4}$$

The quantity m may be calculated directly from the measurement of $I_0$ and $I_t$ using equation (1), while $X_{H2O}$ is available on line 80. Thus, if $X_{Ca}$ and $X_{Ti}$ are also known, the clay content $X_{Clay}$ can be expressed in terms of the equation:

$$X_{Clay}=[m-m_{cell}-X_{Ca}(m_{Ca}-m_{cell})-X_{H2O}(m_{H2O}-m_{cell})-X_{Ti}(m_{Ti}-m_{cell})]/(m_{Clay}-m_{cell}). \tag{5}$$

In a similar manner, the calcium content $X_{Ca}$ and the titanium content $X_{Ti}$ may be expressed in terms of an appropriate set of equations. Thus, the intensity $I_{Ca}$ of the detected calcium fluorescent radiation is governed by the equation:

$$I_{Ca}=\frac{c_1I_0X_{Ca}[1-\exp(-W_b(k_0m_0+k_1m_1))]}{k_0m_0+k_1m_1}, \tag{6}$$

where $I_0$ and $X_{Ca}$ are defined as before, $m_0$ is the absorption coefficient of the web at the incident energy of 5.9 KeV, $m_1$ is the absorption coefficient at the calcium fluorescence energy of 3.7 KeV, and $c_1$, $k_0$, and $k_1$ are constants determined by system geometry. The quantity $m_1$ is derived according to equation (4), computed for the energy of 3.7 KeV, while $m_0$ is determined directly from the preferential absorption measurement using equation (1) as before. Equation (6) may be rewritten as:

$$[X_{Ca}=\frac{I_{Ca}(k_0m_0+k_1m_1)}{C_1I_0[1-\exp(-W_b(k_0m_0+K_1m_1))]}\ ] \tag{7}$$

$$X_{Ca}=\frac{I_{Ca}(k_0m_0+k_1m_1)}{C_1I_0[1-\exp(-W_b(k_0m_0+k_1m_1))]}$$

In an analogous manner, the titanium content of the web 10 can be expressed as:

$$[X_{Ca}=\frac{I_{Ca}(k_0m_0+k_1m_1)}{C_1I_0[1-\exp(-W_b(k_0m_0+k_1m_1))]}\ ] \tag{8}$$

$$X_{Ti}=\frac{I_{Ti}(k_0m_0+k_2m_2)}{C_2I_0[1-\exp(-W_b(k_0m_0+k_2m_2))]},$$

where $X_{Ti}$, $I_0$, $K_0$, $W_b$, and $m_0$ are defined as before, $m_2$ is the absorption coefficient of the web 10 at the titanium fluorescence energy of 4.5 KeV, and $c_2$ and $k_2$ are constants determined by system geometry. The quantity $m_2$ is derived according to equation (4), computed for an energy of 4.5 KeV.

Equations (5), (7), and (8), effectively constitute a system of three simultaneous equations in the three unknowns $X_{Ca}$, $X_{Clay}$, and $X_{Ti}$, the quantities $m_1$ and $m_2$ equations (7) and (8) each being dependent on these unknown quantities. Initially in solving equations (5), (7), and (8), I use zero or some predetermined set point for $X_{Ca}$, $X_{Clay}$ and $X_{Ti}$. From then on trial values of $m_1$ and $m_2$ are determined using the values of $X_{Ca}$, $X_{Clay}$, and $X_{Ti}$ obtained on the previous count. Next, trial values of $X_{Ca}$ and $X_{Ti}$ are determined using equations (7) and (8). After that, a trial value of $X_{Clay}$ is obtained using equation (5). This three-step process is then repeated a sufficient number of times to achieve the desired accuracy.

The iterative steps described above are performed by the signal processing circuit shown in FIG. 3, which is preferably made up of digital components having multibit parallel inputs and outputs. As in FIG. 1, in FIG. 3 I have shown single lines for purposes of clarity. The signal processing circuit includes a preferential absorption determining circuit, indicated generally by the reference character 96. Circuit 96 determines the preferential absorption coefficient $m_0$ from the signals on lines 62, 66, and 74 in accordance with equation (1). More particularly, the transmitted intensity signal on line 62 drives the numerator input of a divider circuit 98, the denominator input of which is responsive to the source intensity signal on line 66. Divider 98 drives a logarithm circuit 100, the output of which is the negative of the natural logarithm of the input. Circuit 100 drives the numerator input of a second divider circuit 102, the denominator input of which is driven by the basis weight signal on line 74. Divider 102 provides the preferential absorption coefficient $m_0$ on line 103.

A clay content determining circuit, indicated generally by the reference numeral 104, determines the clay content $X_{Clay}$ from the absorption coefficient $m_0$ and signals representing the calcium content, the water content, and titanium content, respectively, in accordance with equation (5). More particularly, respective calcium, water, and titanium content signals on lines 155, 80, and 191 drive respective weighting circuits 106, 108, and 110, each of which multiplies the corresponding content signal by a constant corresponding to the difference between the absorption coefficient of that constituent and the absorption coefficient of cellulose. An adder 112 sums the outputs of weighting circuits 106, 108, and 110. Circuit 114 combines the output of adder 112 and a constant representing the absorption coefficient of cellulose. The output of circuit 114, which corresponds to the expected absorption coefficient of the web 10 with the given contents of calcium, titanium, and moisture, is fed to the subtractive input of a subtractor circuit 16 whose additive input is responsive to the signal $m_0$. A circuit 118 divides the output of circuit 116 by a constant corresponding to the difference between the absorption coefficient of clay and that of cellulose. Circuit 118 provides the clay content $X_{Clay}$ on line 119.

A calcium fluorescence absorption calculator, indicated generally by the reference numeral 121, determines the calcium fluorescence absorption coefficient $m_1$ from the constituent contents in accordance with equation (4) for an energy of 3.7 KeV. More particularly, respective weighting circuits 124, 126, 128, and 130 are responsive to the content signals on lines 155, 119, 80, and 191. Each of the weighting circuits 124, 126, 128, and 130 multiplies the corresponding content signal by a constant corresponding to the difference between the absorption coefficient of that constituent and the absorption coefficient of cellulose. A circuit 132 sums the outputs of circuits 124, 126, 128, and 130. The output of circuit 132 is fed to another circuit 134, which combines the output of circuit 132 with a constant corresponding to the absorption coefficient of cellulose. Circuit 134 provides the absorption coefficient $m_1$ on line 135.

A calcium content determining circuit, indicated generally by the reference numeral 122, provides calcium content signal $X_{Ca}$ on line 155 in accordance with equation (7). More particularly, a first circuit multiplies the output of circuit 134 by the constant $k_1$ while a second circuit responsive to the output of divider 102 multiplies the output of that circuit by the constant $k_0$. An adder 140 responsive to the outputs of circuits 136 and 138 drives one input of a first multiplier circuit 142 together with one input of a second multiplier circuit 146. Multiplier circuit 142, which is also responsive to the calcium fluorescence intensity signal on line 44, drives the numerator input of a divider circuit 144. Multiplier circuit 146, which is also responsive to the basis weight signal on line 74, drives an exponential circuit 148 which derives the exponential of the negative of its input. A divider circuit 150 provides as an output the difference between 1 and the output of circuit 148. Circuit 150 drives one input of a multiplier circuit, the other input of which is responsive to the source intensity signal on line 66. Multiplier 152 drives a circuit 154 which multiplies the input by the constant $C_1$. Circuit 154 drives the denominator input of divider 144. Circuit 144 provides the calcium content signal on line 155.

A titanium fluorescence absorption calculator, indicated generally by the reference numeral 157, determines the titanium fluorescence absorption coefficient $m_2$ from the constituent contents in accordance with equation (4) for an energy of 4.5 KeV. Respective weighting circuits 160, 162, 164, and 166, responsive to the content signals on lines 155, 119, 80, and 191, multiply the content signals by constants corresponding to the difference between the absorption coefficient of the constituent and that of cellulose. An adder circuit 168 responsive to the outputs of circuits 160, 162, 164, and 166 provides a sum signal to circuit 170. Circuit 170 combines this signal with a constant corresponding to the absorption coefficient of cellulose to provide the absorption coefficient $m_2$ on line 171.

A titanium content determining circuit, indicated generally by the reference numeral 122, provides a titanium content signal $X_{Ti}$ on line 191 in accordance with equation (8). A first circuit 172 multiplies the output of circuit 170 by the constant $k_2$, while a second circuit 174 multiplies the output of divider circuit 102 by the constant $k_0$. An adder 176 responsive to the output of circuits 172 and 174 provides one input to a first multiplier circuit 178 and to a second multiplier circuit 182. The first multiplier circuit 178, which is also responsive to th titanium fluorescence intensity signal on line 52, drives the numerator input of a divider circuit 180. Multiplier circuit 182, also responsive to the basis weight signal on line 74, drives an exponential circuit 184 which derives the negative exponential of its input. A subtractor circuit 186 subtracts the output of circuit 184 from 1 and provides the difference signal to one input of a multiplier circuit 188. Circuit 188, which is also responsive to the source intensity signal on line 66, drives a circuit 190 which multiplies its input by the constant $C_2$. Circuit 190 drives the denominator input of divider 180. Circuit 180 provides the titanium content signal on line 191.

Circuits 96, 104, 121, 122, 157, and 158 automatically perform the iterative steps by continually providing correcting inputs to one another. The outputs of these circuits thus rapidly converge to final values which satisfy equations (5), (7), and (8), the exact rate of convergence depending on the propagation delays of the particular components used. The additive contents based on a given pulse count are available well before the end of the next count so that the system operates in an on-line, virtually continuous manner. As was stated before, and as is implicit from equations (1) to (8), each of the quantities on lines 119, 155, and 191 is normalized to the actual basis weight of the web 10 provided on line 74. After the content signals have converged to their final values, they may be fed to a suitable control system or transferred to data recorders such as the recorders 120, 156, and 192 shown in FIG. 3.

While I have shown and described a specific embodiment of my invention which involves a measurement of both calcium and titanium additives it will be appreciated that, as a practical matter, in many installations only one of the additives $CaCO_3$ and $TiO_2$ is present in the paper web. In such case, only one fluorescence measurement need be made and the absorption coefficients need only be determined on the basis of those constituents actually present. It is also possible to construct a system which, rather than solving equations (7) and (8) in their exact form, solves a modified form of equations (7) and (8) linearized at the setpoint or desired values. Further, in some applications, rather than relying on continuous on-line measurements, it may be possible to ignore variations in basis weight or moisture content, particularly at the dry end of the paper web. Finally, it is obvious that equivalent computational steps may be performed with a programmed general-purpose computer, using absolute contents rather than fractional contents as basic variables, or with the iterative steps in a different order.

It will be seen that I have accomplished the objects of my invention. My system individually monitors the paper constituents of calcium carbonate, titanium dioxide, and clay, the last of which fluoresces at too low an energy to permit direct fluorescence measurement. My system is insensitive to small variations in the energy level of the radiation source. My system provides compensation for paper properties other than the property being measured.

It will be understood that certain features and subcombinations are of utility and may be employed without reference to other features and subcombinations. This is contemplated by and is within the scope of my claims. It is further obvious that various changes may be made in details within the scope of my claims without departing from the spirit of my invention.

Having thus described my invention, what I claim is:

[1. Apparatus for measuring the contents of a first additive in a sheet material containing a second additive exhibiting high-energy X-ray fluorescence, said apparatus comprising:

means for irradiating the sheet material with X-ray radiation of a sufficiently high energy level to cause said second additive to emit fluorescent radiation;

means responsive to said fluorescent radiation for providing a first signal;

means responsive to radiation penetrating said sheet for providing a second signal; and means responsive to said first and second signals for computing the content of said first additive in said sheet material.]

2. Apparatus as in claim [1] *16* in which said second signal providing means comprises means for measuring the intensity of radiation transmitted from said irradiating means through said sheet material.

[3. Apparatus as in claim 1 in which said content computing means comprises:

means responsive to said first signal for estimating the absorption of said penetrating radiation by said sheet material; and means responsive to said second signal for computing the actual absorption of said penetrating radiation by said sheet material;

means for comparing said actual absorption with said estimated absorption to provide a difference signal; and means responsive to said difference signal for computing the content of said first additive.]

[4. Apparatus as in claim 3, further comprising means responsive to said computed additive content for correcting said estimated absorption.]

[5. Apparatus as in claim 3 in which said absorption estimating means comprises means responsive to said first signal for computing the content of said second additive and means responsive to said computed second additive content for estimating the absorption of said penetrating radiation by said sheet of material.]

6. Apparatus as in claim [5] *16* in which said second additive content computing means is responsive to the computed first additive content.

7. Apparatus as in claim [5] *16* in which said second additive content computing means comprises means responsive to the computed first additive content for computing the absorption of said fluorescent radiation by said sheet of material, and means responsive to said computed fluorescent radiation absorption and to said first signal for computing the content of said second additive.

8. Apparatus as in claim 7 in which said fluorescent radiation absorption computing means is responsive to said computed second additive content.

9. Apparatus as in claim [1] *16*, further comprising means for measuring the total mass per unit area of said sheet of material to provide a third signal and means for normalizing said first and second signals relative to said third signal.

10. Apparatus as in claim [1] *16* in which said irradiating means comprises a 5.9 KeV radiation source.

11. Apparatus as in claim 10 in which said radiation source comprises $^{55}Fe$.

12. Apparatus as in claim [1] *16* in which said additive exhibiting high-energy fluorescence is $CaCO_3$, said first signal providing means being sensitive to radiation of 3.7 KeV.

13. Apparatus as in claim [1] *16* in which said additive exhibiting high-energy fluorescence is $TiO_2$, said first signal providing means being sensitive to a radiation energy of 4.5 KeV.

14. Apparatus as in claim [1] *16* in which said first signal providing means comprises a proportional detector and a pulse height analyzer coupled to said proportional detector.

15. Apparatus as in claim [1] *16* in which said sheet material contains titanium dioxide and calcium carbonate, said first signal providing means comprising a first solid-state detector sensitive to a radiation energy of 4.5 KeV and a second solid-state detector sensitive to a radiation energy of 3.7 KeV.

16. Apparatus for measuring the content of first and second additives in a sheet material, said first additive exhibiting relatively low-energy X-ray fluorescence, said second additive exhibiting relatively high energy X-ray fluorescence, said apparatus comprising:

means for irradiating the sheet material with X-ray radiation of a sufficiently high energy level to cause said second additive to emit fluorescent radiation;

means responsive to said fluorescent radiation for providing a first signal;

means responsive to radiation penetrating said sheet for providing a second signal;

means responsive to said first signal for computing the content of said second additive;

means responsive to said computed content for estimating the absorption of the penetrating radiation by said sheet material;

means responsive to said second signal for computing the actual absorption of the penetrating radiation by said material;

means for comparing the actual absorption with the estimated absorption to provide a difference signal;

means responsive to said difference signal for computing the content of said first additive; and means responsive to said computed first additive content for correcting said computed second additive content.

17. Apparatus as in claim 16 in which said first additive content computing means and said correcting means operate iteratively.

18. Apparatus as in claim 16 in which said sheet material also contains a third additive exhibiting high-energy X-ray fluorescence, said apparatus further comprising:

means responsive to fluorescent radiation from said third additive for providing a third signal;

means responsive to said third signal for computing the content of the third additive;

means responsive to said computed third additive content for correcting the estimated absorption; and means responsive to the computed first additive content for correcting the computed third additive content.

19. Apparatus as in claim 16 in which said second signal providing means is responsive to radiation passing through said sheet from said irradiating means.

* * * * *